(12) United States Patent
Chattoraj et al.

(10) Patent No.: US 10,295,489 B2
(45) Date of Patent: May 21, 2019

(54) DEPOSIT MONITOR

(71) Applicant: Ecolab USA Inc., St. Paul, MN (US)

(72) Inventors: Mita Chattoraj, Warrenville, IL (US); Michael J. Murcia, Dekalb, IL (US); Aseet Mukherjee, Warrenville, IL (US)

(73) Assignee: Ecolab USA Inc., Saint Paul, MN (US)

( * ) Notice: Subject to any disclaimer, the term of this patent is extended or adjusted under 35 U.S.C. 154(b) by 186 days.

(21) Appl. No.: 15/262,807

(22) Filed: Sep. 12, 2016

(65) Prior Publication Data

US 2018/0073996 A1 Mar. 15, 2018

(51) Int. Cl.
*G01K 7/18* (2006.01)
*G01B 21/08* (2006.01)
*G01K 13/02* (2006.01)
*G01N 17/00* (2006.01)
*G01N 25/14* (2006.01)

(52) U.S. Cl.
CPC .......... *G01N 25/14* (2013.01); *G01B 21/085* (2013.01); *G01K 7/18* (2013.01); *G01K 13/02* (2013.01); *G01N 17/008* (2013.01)

(58) Field of Classification Search
CPC .... C02F 2303/20; F18F 19/00; G01N 17/008; G01N 25/18; G01N 15/0606
See application file for complete search history.

(56) References Cited

U.S. PATENT DOCUMENTS

| | | | |
|---|---|---|---|
| 3,724,267 A * | 4/1973 | Zoschak | G01K 17/00 165/11.1 |
| 4,138,878 A | 2/1979 | Holmes | |
| 4,346,587 A * | 8/1982 | Brindak | G01N 33/1893 436/6 |
| 4,383,438 A * | 5/1983 | Eaton | G01N 25/18 374/7 |

(Continued)

FOREIGN PATENT DOCUMENTS

CN 202013330 U 10/2011
FR 2788600 A1 7/2000

(Continued)

OTHER PUBLICATIONS

Mostafa M. Awad, "Influence of Surface Temperature on Surface Fouling—Theoretical Approach", Life Science Journal, 2012.*

(Continued)

*Primary Examiner* — David A Rogers
(74) *Attorney, Agent, or Firm* — Fredrikson & Byron, P.A.

(57) ABSTRACT

Fluid flow systems can include one or more resistance temperature detectors (RTDs) in contact with the fluid flowing through the system. One or more RTDs can be operated in a heating mode and a measurement mode. Thermal behavior of the one or more RTDs can be analyzed to characterize a level of deposit formed on the RTD(s) from the fluid flowing through the system. Characterizations of deposition on RTDs operated at different temperatures can (Continued)

be used to establish a temperature-dependent deposition profile. The deposition profile can be used to determine if depositions are likely to form at certain locations in the fluid flow system, such as at a use device. Detected deposit conditions can initiate one or more corrective actions that can be taken to prevent or minimize deposit formation before deposits negatively impact operation of the fluid flow system.

20 Claims, 8 Drawing Sheets

(56) References Cited

U.S. PATENT DOCUMENTS

| | | | |
|---|---|---|---|
| 4,514,096 A * | 4/1985 | Wynnyckyj | F23M 11/04 122/504.2 |
| 4,671,072 A | 6/1987 | Starck et al. | |
| 4,718,774 A * | 1/1988 | Slough | G01N 17/008 374/33 |
| 4,722,610 A * | 2/1988 | Levert | F28G 15/00 110/185 |
| 4,832,715 A | 5/1989 | Naruse | |
| 4,967,593 A * | 11/1990 | McQueen | G01F 23/248 210/742 |
| 5,248,198 A | 9/1993 | Droege | |
| 5,360,549 A | 11/1994 | Mouche | |
| 5,590,706 A * | 1/1997 | Tsou | F28B 11/00 165/11.1 |
| 5,992,505 A * | 11/1999 | Moon | F28F 27/00 165/11.1 |
| 6,053,032 A | 4/2000 | Kraus et al. | |
| 6,062,069 A * | 5/2000 | Panchal | G01N 17/008 374/7 |
| 6,250,140 B1 | 6/2001 | Kouznetsov et al. | |
| 6,328,467 B1 * | 12/2001 | Keyhani | B64D 15/20 374/16 |
| 6,386,272 B1 * | 5/2002 | Starner | G01B 7/06 165/11.1 |
| 6,432,168 B2 * | 8/2002 | Schonauer | F01N 9/002 55/282.3 |
| 6,499,876 B1 * | 12/2002 | Baginksi | G01N 17/008 374/29 |
| 6,666,905 B2 | 12/2003 | Page et al. | |
| 6,789,938 B2 * | 9/2004 | Sandu | B08B 1/008 15/104.05 |
| 6,886,393 B1 * | 5/2005 | Romanet | F17D 3/01 374/7 |
| 6,960,018 B2 * | 11/2005 | Sandu | B08B 1/008 15/104.05 |
| 7,077,563 B2 * | 7/2006 | Xiao | G01N 17/008 374/10 |
| 7,082,825 B2 | 8/2006 | Aoshima et al. | |
| 7,581,874 B2 * | 9/2009 | Hays | A61L 2/16 374/147 |
| 7,594,430 B2 * | 9/2009 | Beardwood | A61L 2/16 374/7 |
| 8,104,531 B2 * | 1/2012 | Tochon | F28F 3/083 165/11.1 |
| 8,109,161 B2 * | 2/2012 | Jovancicevic | G01N 17/008 73/865.8 |
| 8,147,130 B2 * | 4/2012 | Sakami | G01B 21/085 374/134 |
| 8,274,655 B2 | 9/2012 | Herzog | |
| 8,360,635 B2 * | 1/2013 | Huang | G01F 1/663 374/137 |
| 8,517,600 B2 * | 8/2013 | Wan | G01N 17/008 374/7 |
| 8,672,537 B2 * | 3/2014 | Veau | F28F 19/00 374/147 |
| 8,746,968 B2 * | 6/2014 | Auret | G01N 25/18 374/29 |
| 9,151,204 B2 * | 10/2015 | Hashida | F01N 11/00 |
| 9,176,044 B2 * | 11/2015 | Bosbach | G01N 25/18 |
| 9,207,002 B2 | 12/2015 | Campbell et al. | |
| 9,506,883 B2 * | 11/2016 | Takahashi | G01N 33/1853 |
| 9,939,395 B2 * | 4/2018 | Wolferseder | G01N 25/18 |
| 2001/0013220 A1 * | 8/2001 | Schonauer | F01N 9/002 60/273 |
| 2001/0035044 A1 * | 11/2001 | Larsson | G01N 1/2202 73/28.01 |
| 2001/0051108 A1 * | 12/2001 | Schonauer | G01N 25/22 422/68.1 |
| 2003/0062063 A1 * | 4/2003 | Sandu | B08B 1/008 134/1 |
| 2004/0139799 A1 * | 7/2004 | Sudolcan | G01F 1/696 73/204.17 |
| 2004/0144403 A1 * | 7/2004 | Sandu | B08B 1/008 134/6 |
| 2007/0025413 A1 * | 2/2007 | Hays | A61L 2/16 374/7 |
| 2007/0080075 A1 * | 4/2007 | Wang | G01N 27/4074 205/781 |
| 2008/0190173 A1 * | 8/2008 | Wienand | G01N 15/0656 73/28.01 |
| 2008/0264464 A1 | 10/2008 | Lee et al. | |
| 2008/0291965 A1 | 11/2008 | Wolferseder | |
| 2009/0000764 A1 * | 1/2009 | Tochon | F28F 3/083 165/11.1 |
| 2009/0094963 A1 * | 4/2009 | Mizoguchi | F01N 3/101 60/286 |
| 2009/0260987 A1 * | 10/2009 | Valdes | G01N 27/4073 204/424 |
| 2010/0084269 A1 * | 4/2010 | Wang | C01G 49/009 204/424 |
| 2011/0283773 A1 * | 11/2011 | Suzuki | G01K 7/16 73/25.05 |
| 2011/0283780 A1 | 11/2011 | Bosbach et al. | |
| 2011/0286492 A1 | 11/2011 | Auret et al. | |
| 2011/0310927 A1 * | 12/2011 | Bombardieri | A47L 15/4285 374/185 |
| 2013/0031973 A1 | 2/2013 | Kirst et al. | |
| 2013/0144503 A1 * | 6/2013 | Nishijima | F02D 41/1466 701/102 |
| 2013/0256296 A1 * | 10/2013 | Hocken | G01K 7/16 219/497 |
| 2014/0346041 A1 * | 11/2014 | Nishijima | G01N 27/4067 204/408 |
| 2015/0023393 A1 * | 1/2015 | Britton | G01K 7/24 374/185 |
| 2015/0268078 A1 * | 9/2015 | Zhang | G01F 1/6884 374/45 |
| 2015/0308875 A1 * | 10/2015 | Muller | G01F 1/692 73/204.26 |
| 2015/0355076 A1 * | 12/2015 | Eaton | G01N 17/008 73/61.62 |
| 2016/0017780 A1 * | 1/2016 | Kinugawa | F01N 3/2006 60/286 |
| 2016/0017830 A1 * | 1/2016 | Wienand | G01N 15/0656 73/23.31 |
| 2016/0061691 A1 * | 3/2016 | Stojicevic | G01M 15/102 73/23.31 |

FOREIGN PATENT DOCUMENTS

| | | |
|---|---|---|
| WO | 2000043762 A1 | 7/2000 |
| WO | 2002004290 A1 | 1/2002 |
| WO | 2009135504 A1 | 11/2009 |
| WO | WO 2009-135504 A1 * | 11/2009 |
| WO | 2010087724 A1 | 8/2010 |
| WO | 2013141438 A1 | 9/2013 |

OTHER PUBLICATIONS

Sinčić et al., "Novel Fouling Measurment Device", Chemical and Biochemical Engineering Quarterly, vol. 28, No. 4, 2014.*
Machine translation of WO 2009-135504 A1, which originally published on Nov. 12, 2009.*

(56) References Cited

OTHER PUBLICATIONS

International Patent Application No. PCT/US2017/051108, International Search Report and Written Opinion dated Jan. 2, 2018, 15 pages.
"Introduction to the DATS Fouling Monitor Technology," Bridger Scientific Inc., 2011, 10 pages.
"Tomographic Applications for Oil & Gas Industry," Rocsole Ltd, 2014, 53 pages.

* cited by examiner

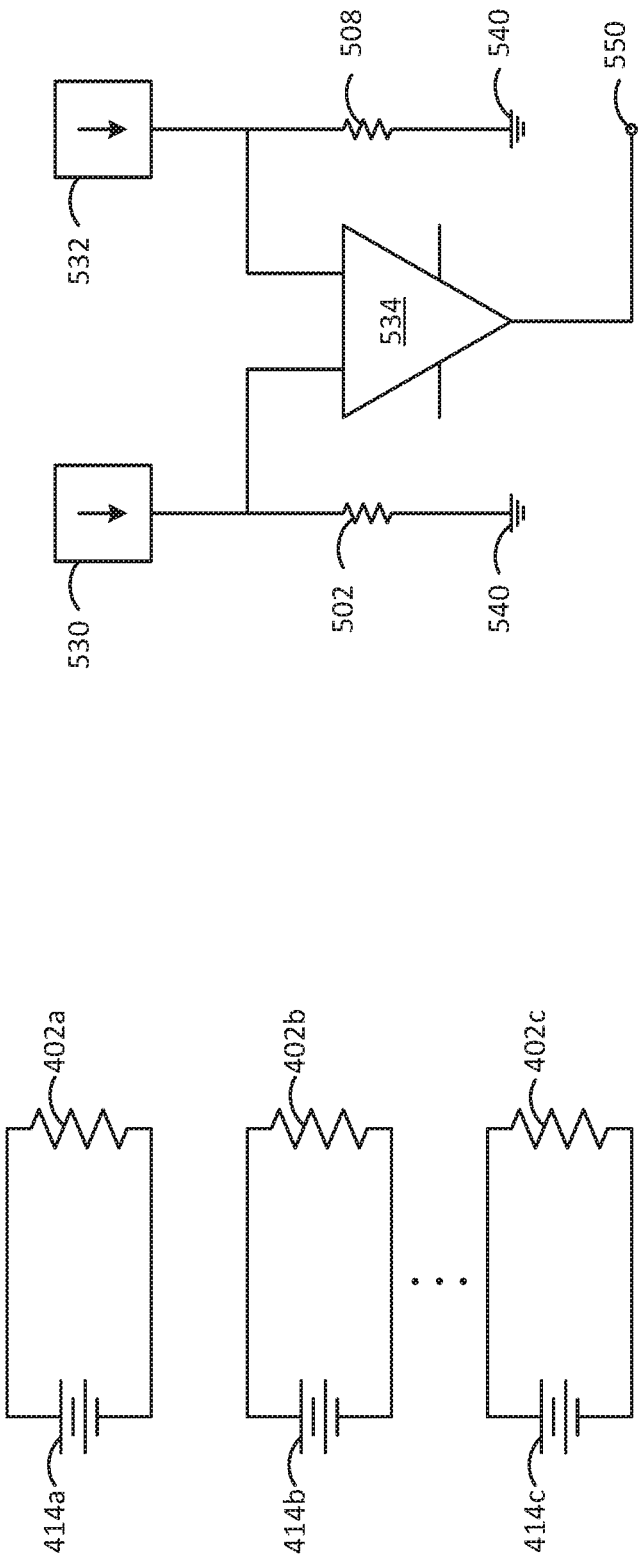

DEPOSIT MONITOR

BACKGROUND

Various fluid flow systems are arranged to flow a process fluid from one or more input fluid sources toward a use device. For example, fluid flowing toward a heat exchanger surface can be used to transfer heat to or draw heat from the heat exchange surface and maintain the surface at an operating temperature.

In some examples, changes in the operating conditions of the fluid flow system, such as changes in the makeup of the fluid, operating temperatures of the fluid or the use device, or the like, can affect the likelihood of deposits forming from the process fluid onto system components. Deposits forming on the use device can negatively impact the performance of the device. For example, deposits forming on the heat exchange surface can act to insulate the heat exchange surface from the fluid, reducing the ability of the fluid to thermally interact with the heat exchanger.

Often, such deposits are detected only when the performance of the use device degrades to the point of requiring attention. For example, a heat exchanger surface can become unable to maintain desired temperatures due to a sufficiently large deposit forming on a heat exchange surface thereof. In order to restore the system to working order, the system often must be shut down, disassembled, and cleaned, which can be a costly and time-consuming process.

SUMMARY

Certain aspects of the disclosure are generally directed to systems and methods for characterizing levels of deposits and/or detecting deposit conditions present in a fluid flow system. Some such systems can include one or more resistance temperature detectors (RTDs) in thermal communication with the fluid flowing through the fluid flow system. The RTD(s) can interface with a heating circuit configured to apply electrical power to the RTD(s), for example, to increase the temperature of the RTD(s). Additionally or alternatively, the RTD(s) can interface with a measurement circuit configured to provide an output representative of the temperature of one or more RTDs.

Systems can include a controller in communication with the heating circuit and the measurement circuit, and can be configured to operate the RTD(s) in a heating mode and a measurement mode. In some examples, the controller can be configured to heat the RTD(s) to an elevated temperature (e.g., in the heating mode), stop heating the RTD(s), and characterize the temperature change of the RTD(s) over time (e.g., in the measurement mode). The characterizing the temperature change of the RTD(s) can include characterizing the temperature change due to thermal conduction of heat from the RTD(s) to the fluid flowing through the flow system via the measurement circuit. Deposits from the fluid flow on the RTD(s) can impact the thermal conduction between the RTD and the fluid. Thus, in some embodiments, the controller can be configured to determine a level of deposit formed on the surface of the RTD(s) from the fluid based on the characterized temperature change.

In some examples, a controller can be configured to periodically switch the RTD(s) between the heating mode and the measurement mode and observe changes in the thermal behavior of the RTD(s). The controller can be configured to characterize a level of deposit from the fluid onto the RTD(s) based on the observed changes.

In some exemplary systems including a plurality of RTDs, the controller can be configured to maintain each of a plurality of RTDs at a different operating temperature and perform such processes on the RTDs. The controller can be configured to determine a temperature-dependent deposition profile based on the characterized levels of deposit of each of the RTDs and determine, based on the profile, if a deposit condition exists for the use device.

In various embodiments, observing changes in the behavior of an RTD can include a variety of observations. Exemplary observations can include changes in the temperature achieved by the RTD when a constant power is applied thereto, changes in the rate of temperature change of the RTD, amount of electrical power applied in the heating mode of operation to achieve a certain temperature, and the like. Each such characteristic can be affected by deposits forming on the RTD from the fluid, and can be used to characterize the level of deposit on the RTD.

In some examples, corrective actions can be taken to address detected deposits and/or deposit conditions. For example, changes to the fluid flowing through the system can be adjusted to minimize the formation of deposits. Such changes can include adding a chemical such as a scale inhibitor or a biocide to reduce deposit formation or stopping the flow of certain fluids into the system that may be contributing to deposit formation. Other corrective actions can include changing system parameters, such as fluid or use device operating temperatures. In some embodiments, such corrective actions can be performed manually by a system operator. Additionally or alternatively, such actions can be automated, for example, via the controller and other equipment, such as one or more pumps, valves, or the like. In still further examples, the system can be configured to perform a corrective action in the form of alerting a user of deposit conditions so that the user can take subsequent corrective actions.

BRIEF DESCRIPTION OF THE DRAWINGS

FIG. 4 is a schematic diagram showing operation of a plurality of RTDs in a heating mode of operation.

FIG. 5 is a schematic diagram showing operation of a single of RTDs in a measurement mode of operation.

DETAILED DESCRIPTION

A resistance temperature detector (RTD) is a device commonly used to measure the temperature of an object of interest. For example, in some instances, the resistance of the RTD is approximately linear with respect to temperature. The resistance can be measured by passing a current through the RTD and measuring the resulting voltage across the RTD. A current flowing through the RTD can have heating effects on the RTD, so the current is typically maintained at a relatively low magnitude during a temperature measurement. In exemplary operation, a small amount of current is passed through a conductor that is exposed to some environment where temperature is to be measured. As temperature changes, the characteristic change in resistance in that conductor (e.g., platinum) is measured and used to calculate the temperature.

Figure 1:
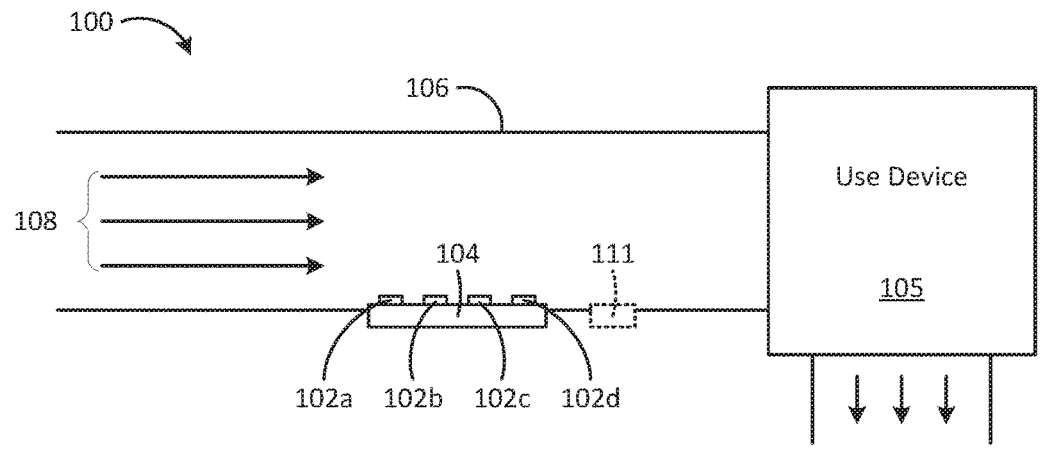
FIG. 1 is an illustration of an exemplary placement of one or more RTDs in a fluid flow system.

FIG. 1 is an illustration of an exemplary placement of one or more RTDs in a fluid flow system. As shown, RTDs 102a-d are positioned in the flow path 106 of a process fluid in a fluid flow system 100 configured to direct a process fluid to a use device 105. Arrows 108 illustrate an exemplary flow path of fluid from a fluid source toward the use device 105. As described herein process fluids can generally relate to any fluids flowing through such a fluid flow system, including but not limited to utility fluids such as cooling water, boiler feed water, condensate, blowdown water, waste water, and discharged effluent water. Such exemplary process fluids can be directed into the fluid flow system 100 from a variety of sources (e.g., an effluent stream from a process, boiler blowdown water, treated waste water, produced water, a fresh water source, etc.). In some examples, a single fluid flow system 100 can receive input process fluids from a variety of sources. In some such examples, the source of process fluid can be selected, such as via a manual and/or automated valve or series of valves. In some embodiments, a single fluid source can be selected from one or more possible input sources. In alternative embodiments, a plurality of fluid sources can be selected such that fluid from the selected plurality of sources is mixed to form the input fluid. In some implementations, a default input fluid is made up of a mixture of fluids from each of the plurality of available input sources, and the makeup of the input fluid can be adjusted by blocking the flow of one or more such input sources into the system.

In the example of FIG. 1, RTDs 102a-d are shown as an array of RTDs mounted on a sample holder 104. In some examples, sample holder 104 is removable from the flow path 106 of the fluid flow system 100, for example, to facilitate cleaning, replacing, or other maintenance of RTDs 102a-d. Additionally or alternatively, one or more RTDs (e.g. positioned on a sample holder) can be positioned in the flow path of one or more fluid inputs that contribute to the makeup of the fluid flowing through the fluid flow system 100 to the use device 105. The fluid flow system can be any system in which a process fluid flows, including for example, washing systems (e.g., warewashing, laundry, etc.), food and beverage systems, mining, energy systems (e.g., oil wells, refineries, etc.), air flow through engine air intakes, heat exchange systems such as cooling towers or boilers, pulp and paper processes, and others. Arrows 108 indicate the direction of flow of the fluid past the RTDs 102, which can be used to monitor the temperature of the fluid, and toward the use device 105.

In some embodiments, a fluid flow system comprises one or more additional sensors 111 (shown in phantom) capable of determining one or more parameters of the fluid flowing through the system. In various embodiments, one or more additional sensors 111 can be configured to determine flow rate, temperature, pH, alkalinity, conductivity, and/or other fluid parameters, such as the concentration of one or more constituents of the process fluid. While shown as being a single element positioned downstream of the RTDs 102a-d, one or more additional sensors 111 can include any number of individual components, and may be positioned anywhere in the fluid flow system 100 while sampling the same fluid as RTDs 102a-d.

Figure 2:
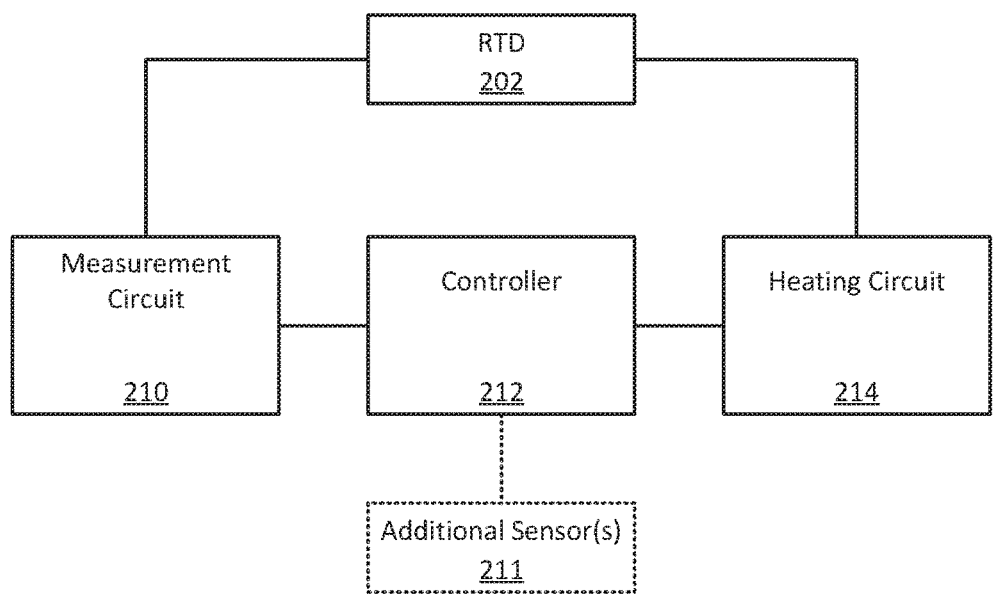
FIG. 2 is a schematic diagram of a system for operating an RTD in an exemplary embodiment.

FIG. 2 is a schematic diagram of a system for operating an RTD in an exemplary embodiment. In the embodiment of FIG. 2, an RTD 202 is in communication with a measurement circuit 210. In some examples, the measurement circuit 210 can facilitate the measurement of the resistance of the RTD in order to determine the temperature thereof. For instance, in an exemplary embodiment, the measurement circuit can provide a current to flow through the RTD and measure the voltage drop across the RTD to determine the resistance, and thus the temperature, thereof.

The system can include a controller 212 in communication with the measurement circuit 210. The controller 212 can include a microcontroller, a processor, memory comprising operating/execution instructions, a field programmable gate array (FPGA), and/or any other device capable of interfacing and interacting with system components. In some such examples, the system can operate in a measurement mode in which the controller 212 can interface with the measurement circuit 210 for determining a temperature of the RTD 202. In some examples, the controller can cause a current to be applied to the RTD via the measurement circuit 210, receive a signal from the measurement circuit 210 representative of the voltage across the RTD 202, and determine the resistance of the RTD based on the known current and measured voltage. In some embodiments, the controller 212 is configured to otherwise determine the resistance and/or the temperature of the RTD 202 based on the signal received from the measurement circuit. Thus, in some such examples, the controller 212 can interface with the measurement circuit 210 and the RTD 202 to determine the temperature of the RTD 202.

The system of FIG. 2 further comprises a heating circuit 214 in communication with the controller 212 and the RTD 202. In some examples, system can operate in a heating mode in which the controller 212 can apply electrical power to the RTD 202 via the heating circuit 214 in order to elevate the temperature of the RTD 202. In some such embodiments, the controller 212 is capable of adjusting or otherwise controlling the amount of power applied to the RTD 202 in order to elevate the temperature of the RTD 202. In various examples, adjusting the applied power can include adjusting a current, a voltage, a duty cycle of a pulse-width modulated (PWM) signal, or other known methods for adjusting the power applied to the RTD 202.

In some examples, the controller 212 is capable of interfacing with the RTD 202 via the heating circuit 214 and the measurement circuit 210 simultaneously. In some such examples, the system can simultaneously operate in heating mode and measurement mode. Similarly, such systems can operate in the heating mode and in the measurement mode independently, wherein the RTD may be operated in the heating mode, the measurement mode, or both simultaneously. In other examples, the controller 212 can switch between a heating mode and a measurement mode of operation. Additionally or alternatively, a controller in communication with a plurality of RTDs 202 via one or more measurement circuits 210 and one or more heating circuits 214 can operate such RTDs in different modes of operation. In various such examples, the controller 212 can operate each RTD in the same mode of operation or separate modes of operation, and/or may operate each RTD individually, for example, in a sequence. Many implementations are possible and within the scope of the present disclosure.

As described with respect to FIG. 1, the system can include one or more additional sensors 211 for determining one or more parameters of the fluid flowing through the fluid flow system. Such additional sensors 211 can be in wired or wireless communication with the controller 212. Thus, in some embodiments, the controller 212 can be configured to interface with both RTDs 202 and additional sensors 211 positioned within the fluid flow system.

Figure 3:
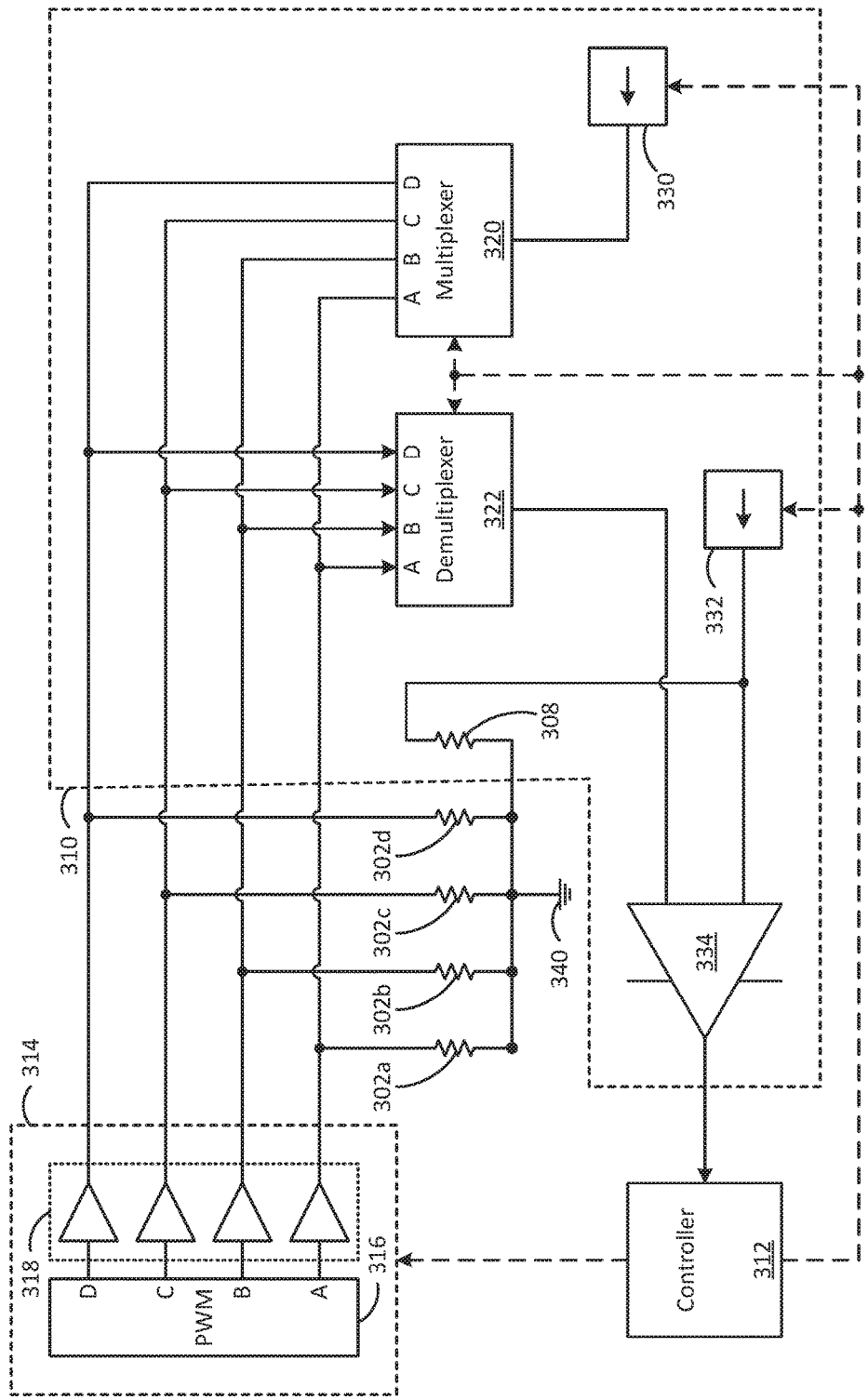
FIG. 3 is an exemplary schematic diagram showing an operational configuration of an array of RTDs.

FIG. 3 is an exemplary schematic diagram showing an operational configuration of an array of RTDs. In the illustrated embodiment, a series of RTDs 302a-d are in communication with a controller 312 via a measurement circuit 310 and a heating circuit 314. During a heating mode of operation, the controller 312 can cause the heating circuit 314 to provide electrical power to one or more of the RTDs 302a-d to elevate the temperature of the RTD. In the illustrated embodiment, the heating circuit 314 includes a PWM module 316 in communication with an amplification stage 318. In the example of FIG. 3, the PWM module 316 includes a plurality of channels A-D, each channel corresponding to a respective RTD 302a-d in the series of RTDs. Each channel of the PWM module 316 is in communication with its corresponding RTD 302a-d via the amplification stage 318. The amplification stage 318 can be configured to modify the signal from the PWM module 316 to generate a heating signal applied to the respective RTD 302a-d. In some examples, the amplification stage 318 is configured to filter a PWM signal from the PWM module 316, for example, via an LRC filter, in order to provide a steady power to the RTD 302. Additionally or alternatively, the amplification stage 318 can effectively amplify a signal from the PWM module 316 for desirably changing the temperature of the RTD 302.

In an exemplary heating operation embodiment, the controller signals the PWM module 316 to elevate the temperature of an RTD 302a. The controller 312 can cause the PWM module 316 to output a PWM signal from channel A to the amplification stage 318. Aspects of the PWM signal, such as the duty cycle, magnitude, etc. can be adjusted by the controller 312 to meet desired heating effects. Additionally or alternatively, the amplification stage 318 can adjust one or more aspects of channel A of the PWM signal to effectively control the amount of heating of the RTD 302a. Similar heating operations can be performed for any or all of RTDs 302a-d simultaneously. In some embodiments, the controller 312 can control heating operation of each of a plurality of RTDs 302a-d such that each of the RTDs is elevated to a different operating temperature.

As described elsewhere herein, the controller 312 can be capable of interfacing with one or more RTDs 302a-d via a measurement circuit 310. In some such examples, the controller 312 can determine, via the measurement circuit 310, a measurement of the temperature of the RTD 302a-d. Since the resistance of an RTD is dependent on the temperature thereof, in some examples, the controller 312 can be configured to determine the resistance of the RTD 302a-d and determine the temperature therefrom. In the illustrated embodiment, the measurement circuit 310 comprises a current source 330 (e.g., a precision current source) capable of providing a desired current through one or more of the RTDs 302a-d to ground 340. In such an embodiment, a measurement of the voltage across the RTD 302a-d can be combined with the known precision current flowing therethrough to calculate the resistance, and thus the temperature, of the RTD 302a-d. In some examples, the current provided to the RTDs from the current source 330 is sufficiently small (e.g., in the microamp range) so that the current flowing through the RTD does not substantially change the temperature of the RTD.

In configurations including a plurality of RTDs 302a-d, the controller 312 can interface with each of the RTDs 302a-d in a variety of ways. In the exemplary embodiment of FIG. 3, the measurement circuit 310 comprises a multiplexer 320 in communication with the controller 312, the current source 330 and the RTDs 302a-d. The controller 312 can operate the multiplexer 320 so that, when a measurement of the voltage across one of the RTDs (e.g., 302a) is desired, the multiplexer 320 directs the current from the current source 330 through the desired RTD (e.g., 302a). As shown, the exemplary multiplexer 320 of FIG. 3 includes channels A, B, C, and D in communication to RTDs 302a, 302b, 302c, and 302d, respectively. Thus, when measuring the temperature of a particular one of RTDs 302a-d, the controller 312 can cause current to be supplied from the current source 330 and through the appropriate channel of the multiplexer 320 and through the desired RTD 302a-d to ground 340 in order to cause a voltage drop thereacross.

In order to measure the voltage drop across a desired one of the plurality of RTDs 302a-d, the measurement circuit 310 includes a demultiplexer 322 having channels A, B, C, and D corresponding to RTDs 302a, 302b, 302c, and 302d, respectively. The controller 312 can direct the demultiplexer 322 to transmit a signal from any one of respective channels A-D depending on the desired RTD. The output of the demultiplexer 322 can be directed to the controller 312 for receiving the signal indicative of the resistance, and therefore the temperature, of a desired RTD. For example, in some embodiments, the output of the demultiplexer 322 does not connect or otherwise has high impedance to ground. Accordingly, current flowing to an RTD (e.g., 302a) via a respective multiplexer 320 channel (e.g., channel A) will only flow through the RTD. The resulting voltage across the RTD (e.g., 302a) will similarly be present at the respective input channel (e.g., channel A) of the demultiplexer 322, and can be output therefrom for receiving by the controller 312. In some examples, instead of being directly applied to controller 312, the voltage across the RTD (e.g., 302a) at the output of the demultiplexer 322 can be applied to a first input of a differential amplifier 334 for measuring the voltage. The amplifier 334 can be used, for example, to compare the voltage at the output of the demultiplexer 322 to a reference voltage before outputting the resulting amplification to the controller 312. Thus, as described herein, a signal output from the demultiplexer 322 for receiving by the controller 312 can, but need not be received directly by the controller 312. Rather, in some embodiments, the controller 312 can receive a signal based on the signal at the output of the demultiplexer 322, such as an output signal from the amplifier 334 based on the output signal from the demultiplexer 322.

In some examples, the measurement circuit 310 can include a reference resistor 308 in line between a second current source 332 and ground 340. The current source 332 can provide a constant a known current through the reference resistor 308 of a known resistance to ground, causing a constant voltage drop across the reference resistor 308. The constant voltage can be calculated based on the known current from the current source 332 and the known resistance of the reference resistor 308. In some examples, the reference resistor 308 is located in a sensor head proximate RTDs 302a-d and is wired similarly to RTDs 302a-d. In some such embodiments, any unknown voltage drop due to unknown resistance of wires is for the reference resistor 308 and any RTD 302a-d is approximately equal. In the illustrated example, reference resistor 308 is coupled on one side to ground 340 and on the other side to a second input of the differential amplifier 334. Thus, the current source 332 in combination with the reference resistor 308 can act to provide a known and constant voltage to the second input of the differential amplifier 334 (e.g., due to the reference resistor 308, plus the variable voltage due to the wiring). Thus, in some such examples, the output of differential amplifier 334 is unaffected by wiring resistance, and can be fed to the controller 312.

As shown in the illustrated embodiment and described herein, the differential amplifier 334 can receive the voltage across the RTD (e.g., 302a) from the output of the demultiplexer 322 at one input and the reference voltage across the reference resistor 308 at its other input. Accordingly, the output of the differential amplifier 334 is indicative of the voltage difference between the voltage drop across the RTD and the known voltage drop across the reference resistor 308. The output of the differential amplifier 334 can be received by the controller 312 for ultimately determining the temperature of the RTD (e.g., 302a). It will be appreciated that, while an exemplary measurement circuit is shown in FIG. 3, measuring the temperature of the RTD could be performed in any variety of ways without departing from the scope of this disclosure. For example, the voltage drop across the RTD could be received directly by the controller 312 as an analog input signal. Additionally or alternatively, a relaxation time of an RC circuit having a known capacitance, C, and a resistance, R, being the resistance of the RTD can be used to determine the resistance of the RTD. In some such examples, such a measurement can eliminate any resistance effect of any wires without using a reference (e.g., reference resistor 308).

In some embodiments, the controller 312 can operate the multiplexer 320 and the demultiplexer 322 in concert so that it is known which of the RTDs is being analyzed. For instance, with respect to the illustrative example of FIG. 3, the controller 312 can operate the multiplexer 320 and the demultiplexer 322 on channel A so that the current from current source 330 flows through the same RTD 302a that is in communication with the differential amplifier 334 via the demultiplexer 322.

In an exemplary configuration such as shown in FIG. 3, in which a plurality of RTDs 302a-d are in communication with different channels of the multiplexer 320 and the demultiplexer 322, the controller 312 can act to switch operating channels of the multiplexer 320 and demultiplexer 322 in order to perform temperature measurements of each of the RTDs 302a-d. For instance, in an exemplary embodiment, the controller can cycle through respective multiplexer 320 and demultiplexer 322 channels in order to perform temperature measurements of each of the respective RTDs 302a-d.

As described elsewhere herein, in some examples, the controller 312 can control heating operation of one or more RTDs. In some such embodiments, the controller 312 stops heating an RTD prior to measuring the temperature of the RTD via the multiplexer 320 and demultiplexer 322. Similarly, when heating an RTD via the heating circuit 314, the controller 312 can turn off the channel(s) associated with that RTD in the multiplexer 320 and demultiplexer 322. In some embodiments, for each individual RTD, the controller 312 can use the heating circuit 314 and the measurement circuit 310 (including the multiplexer 320 and demultiplexer 322) to switch between distinct heating and measurement modes of operation.

FIG. 4 is a schematic diagram showing operation of a plurality of RTDs in a heating mode of operation. As shown, each of a plurality of RTDs 402a-c is in communication with a respective power source 414a-c. As described with reference to FIG. 3, in some examples, each RTD 402a-c is not affected by any measurement circuit components while operating in the heating mode. Thus, each RTD 402a-c can be individually and independently heated via power sources 414a-c. While shown as being DC power sources in the embodiment of FIG. 4, it will be appreciated that any of a variety of adjustable power sources can be used. In some examples, the power source 414a-c comprises a PWM signal filtered and smoothed to provide a substantially DC signal. While shown as being separate power sources 414a-c, in some embodiments, a single component can be used to independently provide adjustable power to each RTD 402a-c.

FIG. 5 is a schematic diagram showing operation of a single of RTDs in a measurement mode of operation. In the illustrated embodiment, a current source 530 is configured to provide a constant current flow through RTD 502 to ground 540. The voltage drop across the RTD 502 is applied to a first input of an amplifier 534. A current source 532 is configured to provide a constant current flow through a reference resistor 508 to ground 540. As described elsewhere herein, the known current from the current source 532 and the known resistance of the reference resistor 508 can be used to determine the voltage drop across the reference resistor 508, which is applied at a second input of the amplifier 534. The output 550 of the amplifier 534 can provide information regarding the difference between the known voltage drop across the reference resistor 508 and the voltage drop across the RTD 502, which can be used to determine the voltage drop across the RTD 502. The determined voltage drop across the RTD 502 can be used with the known current from current source 530 to determine the resistance, and therefore the temperature, of the RTD 502. While not shown in the embodiment of FIG. 5, in some instances, the RTD 502 is a single RTD selected from an array of RTDs, for example, via the operation of a multiplexer and demultiplexer such as shown in FIG. 3.

Referring back to FIG. 1, a plurality of RTDs 102a-d can be disposed in the flow path of a process fluid in a fluid flow system. In some instances, the process fluid may include constituents that form deposits (e.g., scale, biofilm, etc.) on various fluid flow system components, such as the walls of the flow path 106, sensors, process instruments (e.g., a use device 105 toward which the process fluid flows), and the like. In some examples, deposits that form on the RTDs 102a-d in the fluid flow path can act as an insulating layer between the RTD and the process fluid, which can affect the thermal behavior of the RTDs.

Accordingly, in some examples, observing the thermal behavior of one or more RTDs in the fluid flow path can provide information regarding the level of deposit present at the RTDs (e.g., 102a-d). FIGS. 6A-6D illustrate exemplary thermal behavior of an RTD that can be used to characterize the level of deposit at the RTD.

Figure 6A:
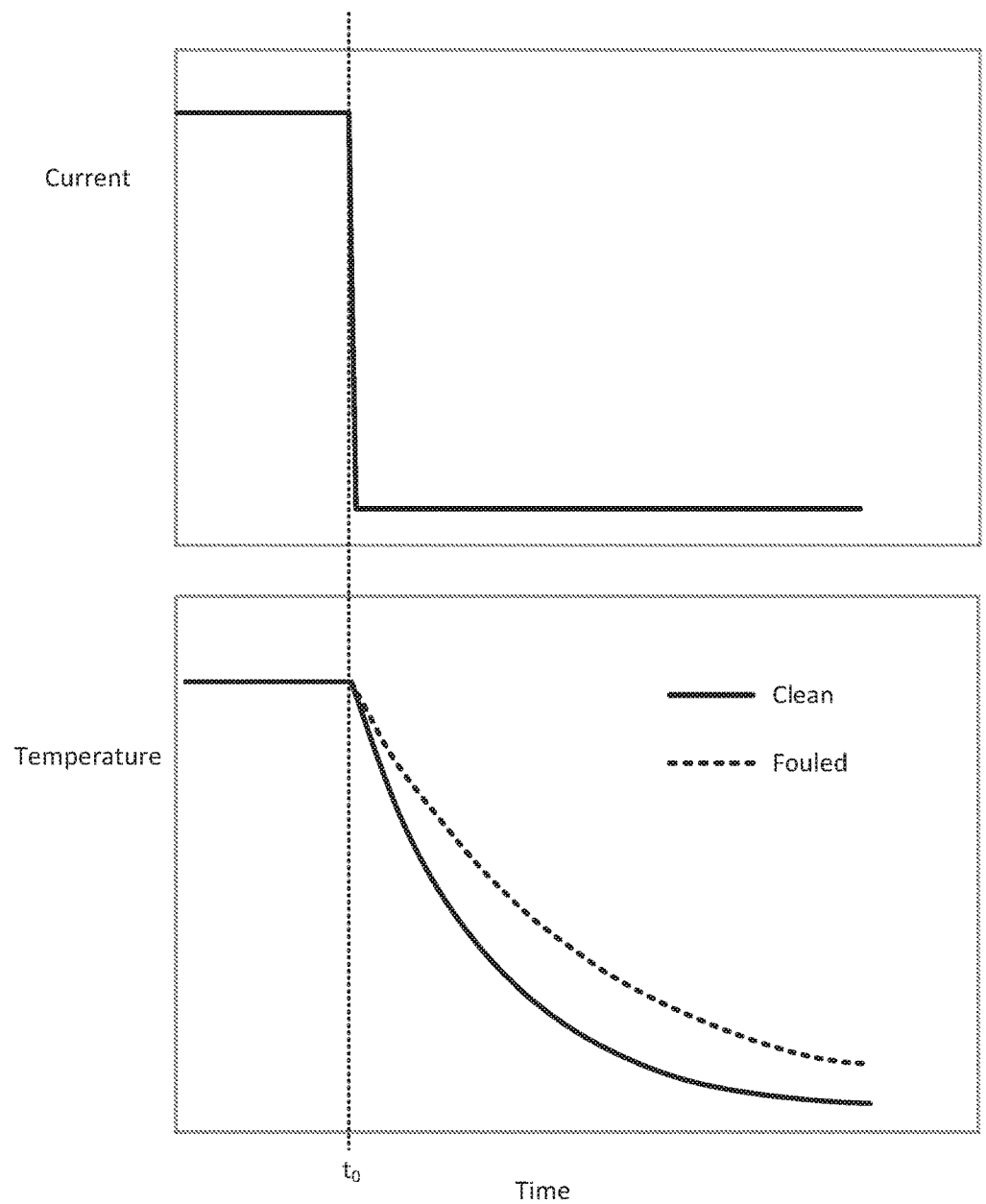
FIGS. 6A-6D illustrate exemplary thermal behavior of an RTD that can be used to characterize the level of deposit at the RTD.

FIG. 6A shows a plot of temperature and current vs time. In the illustrated example, a high current is applied to an RTD (e.g., a smoothed DC current applied to RTD 302a via channel A of the heating circuit 314 of FIG. 3). The applied current heats the RTD to an elevated temperature. At time $t_0$, the current is reduced, and the temperature of the RTD begins to decline. In the illustrated example, the temperature profile of both clean (solid line) and fouled (broken line) RTDs are shown. Though each RTD is heated to a high temperature (not necessarily the same temperature), the clean RTD cools more quickly than the fouled (coated) RTD, since the deposit on the fouled RTD provides thermal insulation between the RTD and the process fluid. In some embodiments, the temperature decay profile can be analyzed to determine the amount of deposit present on the RTD.

With reference to FIG. 2, the controller 212 can heat the RTD 202 via the heating circuit 214. In some examples, the controller 212 can periodically switch to measurement mode to measure the temperature of the RTD 202 via the measurement circuit 210. At time $t_0$, the controller 212 ceases applying power to the RTD 202 via the heating circuit 214 and switches to measurement mode to monitor the temperature of the RTD 202 via the measurement circuit 210 as the temperature decays due to the process fluid. The decay profile of the temperature of the RTD 202 can be monitored by the controller 212 via the measurement circuit 210. In some examples, the controller 212 is configured to analyze the temperature decay profile to determine the level of deposit on the RTD 202. For instance, the controller 212 can fit the decay profile to a function such as an exponential function having a time constant. In some such examples, the fitting parameters can be used to determine the level of deposit.

In an exemplary embodiment, the temperature decay profile over time can be fit to a double exponential function. For example, in some instances, a first portion of the double exponential decay model can represent temperature change due to the process fluid flowing through the flow system. A second portion of the double exponential decay model can represent temperature conductivity from a heated RTD to other components, such as wires, a sample holder (e.g., 104 in FIG. 1) or other components. In some such embodiments, the double exponential fitting functions can independently represent both sources of temperature conduction in the same function, and can be weighted to reflect the relative amount and timing of such temperature changes. In some such examples, a fitting parameter in the first portion of the double exponential decay model is representative of the level of deposit on the surface of an RTD interfacing with the fluid. Thus, in some such embodiments, the second portion of the exponential does not contribute to the characterized level of deposit. It will be appreciated that other fitting functions can be used in addition or alternatively to such a double exponential function.

In some cases, using certain fitting functions in characterizing the deposit can be skewed if the RTD is allowed to reach equilibrium with the process fluid, after which it stops changing in temperature. Accordingly, in various embodiments, the controller 212 is configured to resume heating the RTD prior to the RTD reaching thermal equilibrium and/or to stop associating collected temperature data with the thermal decay profile of the RTD prior to the RTD reaching equilibrium with the process fluid. Doing so prevents non-decay data from undesirably altering the analysis of the thermal decay profile of the RTD. In other embodiments, the fitting function can account for equilibration of the RTD temperature and the process fluid temperature without skewing the fitting function. In some such embodiment, the type of fitting function and/or weighting factors in the fitting function can be used to account for such temperature equilibration.

In some embodiments, the difference in decay profiles between clean and fouled RTDs can be used to determine the level of deposit on the fouled RTD. The decay profile of the clean RTD can be recalled from memory or determined from an RTD known to be free from deposit. In some instances, a fitting parameter such as a time constant can be temperature-independent. Thus, in some such embodiments, it is not necessary that the clean and fouled RTD are elevated to the same temperature for comparing aspects of their thermal decay profiles.

Figure 6B:
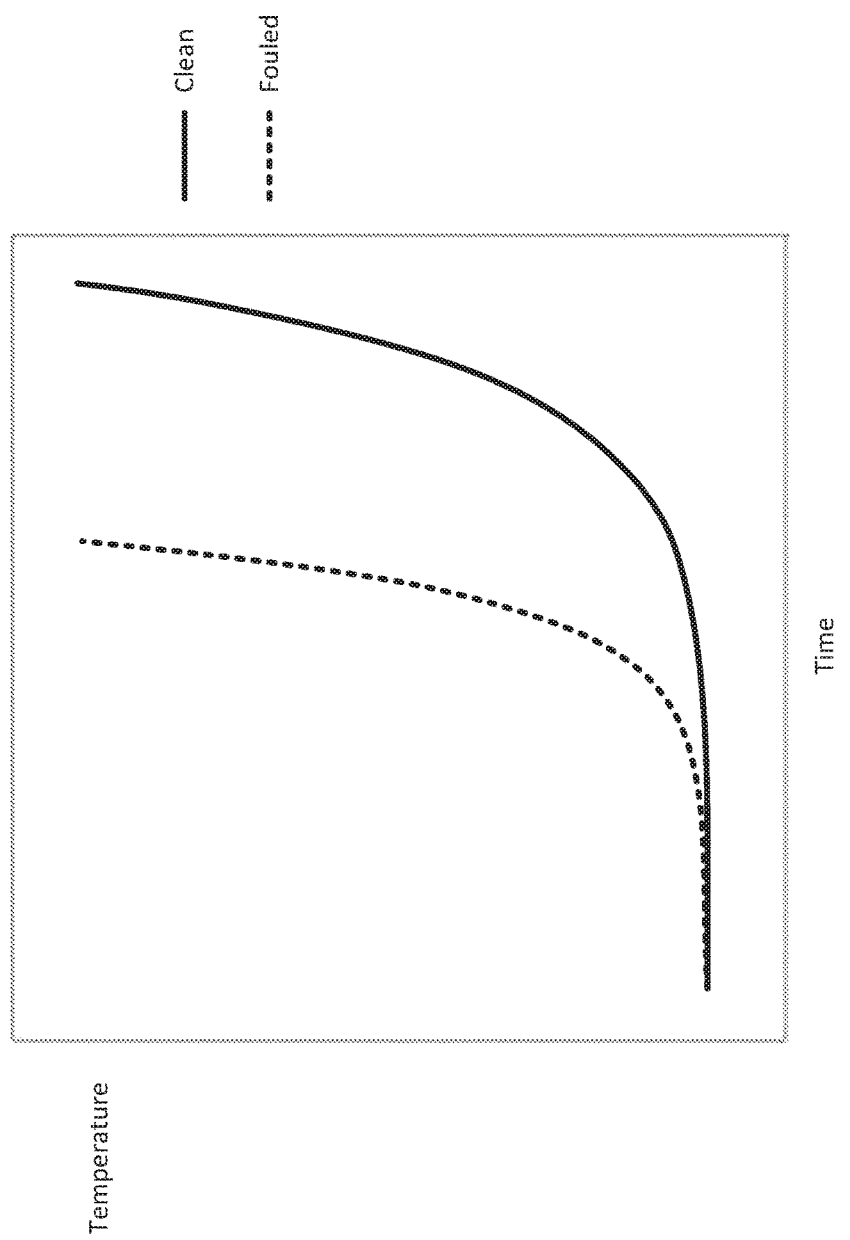

FIG. 6B shows a plot of temperature vs. time. In the illustrated example, an RTD is heated from a steady state condition (e.g., thermal equilibrium with the process fluid) while the temperature is monitored. As opposed to the temperature monitoring of FIG. 6A, in which the temperature can be continuously monitored since the temperature is decaying from an elevated temperature, monitoring the temperature of the RTD while increasing the temperature as in FIG. 6B requires heating of the RTD. Accordingly, in some embodiments, in order to achieve a plot such as that shown in FIG. 6B, the RTD can be rapidly switched from the heating mode to the measurement mode and back to the heating mode in order to achieve a nearly instantaneous temperature measurement while the temperature of the RTD does not significantly change due to the process fluid. In such a procedure, the temperature of the RTD can be elevated via the heating circuit and periodically sampled via the measurement circuit in order to determine a heating profile of the RTD over time.

Similar to FIG. 6A discussed above, the plot of FIG. 6B includes two curves—one representative of a clean RTD (solid line) and one representative of a fouled RTD (broken line). As shown, the fouled RTD increases in temperature much more quickly than the clean RTD, since the deposit on the fouled RTD insulates the RTD from the cooling effects of the process fluid. Thus, in some examples, the heating profile of the RTD can be used to determine a level of deposit on the RTD, for example, by fitting the heating profile to a function.

Figure 6C:
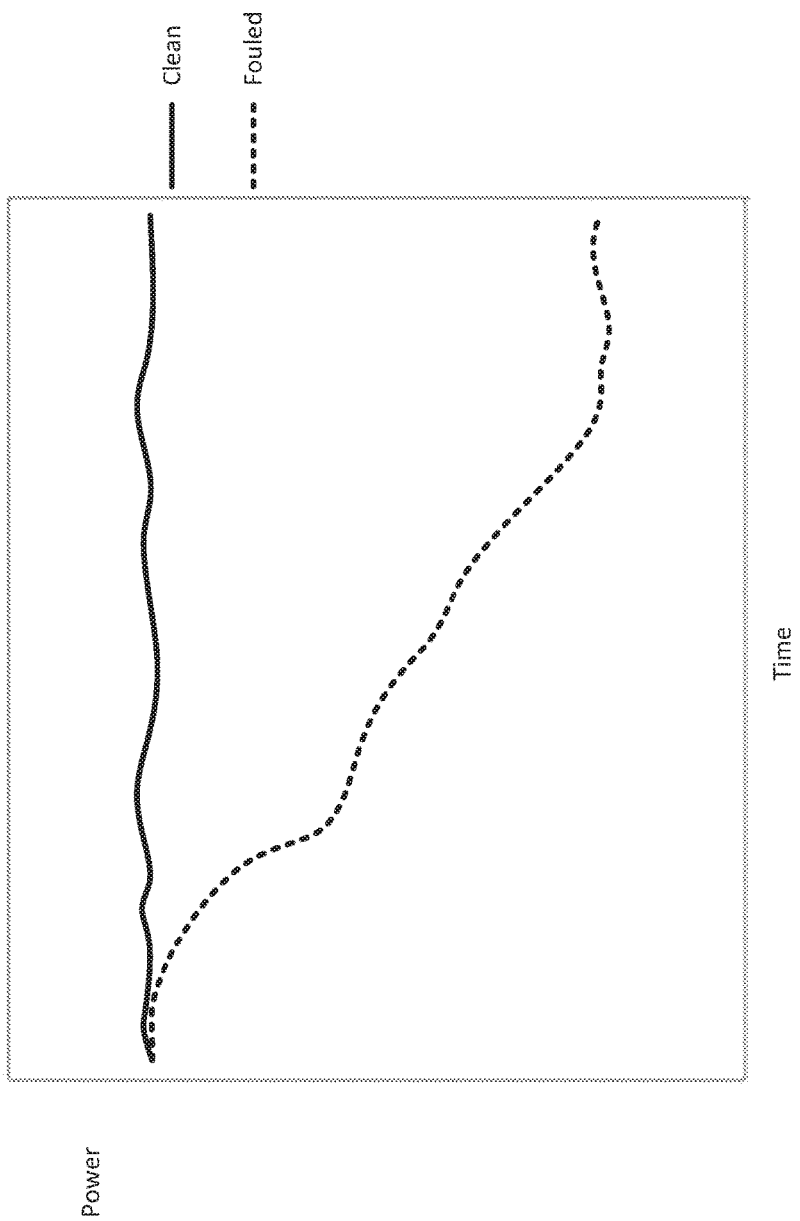

In some embodiments, rather than observing properties regarding RTD temperature change, an RTD can be raised to a fixed operating temperature. FIG. 6C shows a plot of the power required to maintain an RTD at a constant temperature over time. As shown, the power required to maintain a clean RTD (solid line) at a constant temperature remains relatively constant over time, as the RTD and process fluid reach an equilibrium condition. However, if deposits form on the RTD over time (as shown in the broken line representing a fouled RTD), the insulating properties of the deposit shield the RTD from the cooling effects of the process fluid. Thus, as the deposit forms over time, less power is required to be applied to the RTD in order to maintain a constant temperature.

With reference to FIG. 3, in some embodiments, the controller 312 is configured to heat an RTD (e.g., 302a) via the heating circuit 314. The controller 312 can periodically measure the temperature of the RTD (e.g., 302a) via the measurement circuit 310 as a way of providing feedback for the heating circuit 314 operation. That is, the controller 312 can determine the temperature of the RTD (e.g., 302a) via the measurement circuit and adjust the power applied to the RTD (e.g., 302a) via the heating circuit 314 accordingly to achieve and maintain a desired temperature at the RTD. In some such embodiments, the controller switches between the heating mode to the measurement mode and back rapidly so that the temperature of the RTD does not significantly change while measuring the temperature. In various examples, the controller 312 can determine how much power is being applied to the RTD (e.g., 302a), for example, via a magnitude, duty cycle, or other parameter applied from one or more components of the heating circuit 314 (e.g., the PWM module 316 and/or the amplification stage 318) controlled by the controller 312.

In some examples, the amount of power required to maintain the RTD at a fixed temperature is compared to the power required to maintain a clean RTD at the fixed temperature. The comparison can be used to determine the level of deposit on the RTD. Additionally or alternatively, the profile of the required power to maintain the RTD at the fixed temperature over time can be used to determine the level of deposit on the RTD. For instance, the rate of change in the power required to maintain the RTD at the fixed temperature can be indicative of the rate of deposition of the deposit, which can be used to determine the level of a deposit after a certain amount of time.

In another embodiment, an RTD can be operated in the heating mode by applying a constant amount of power to the RTD via the heating circuit and observing the resulting temperature of the RTD. For instance, during exemplary operation, the controller can provide a constant power to an RTD via the heating circuit and periodically measure the temperature of the RTD via the measurement circuit. The switching from the heating mode (applying constant power) to the measurement mode (to measure the temperature) and back to the heating mode (applying constant power) can be performed rapidly so that the temperature of the RTD does not significantly change during the temperature measurement.

Figure 6D:
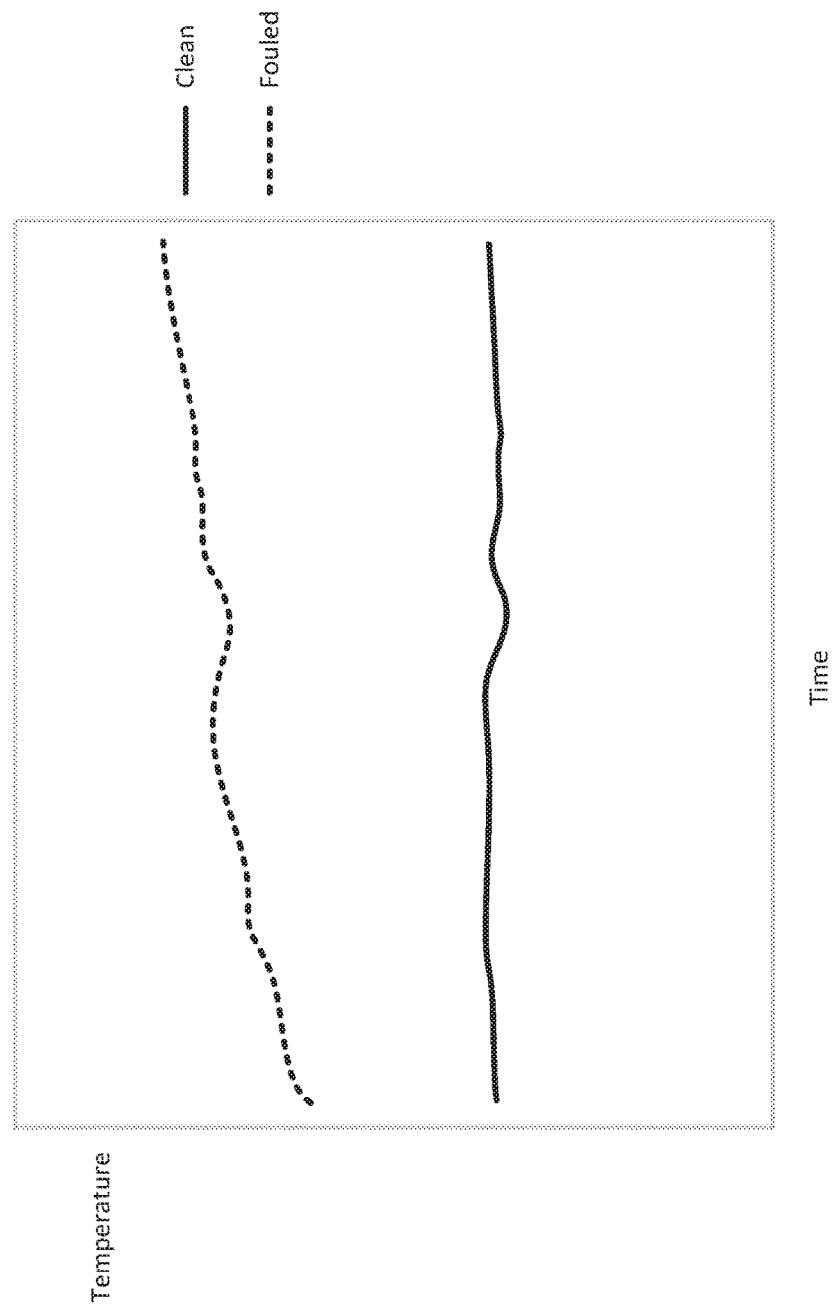

FIG. 6D is a plot of temperature vs time of an RTD to which a constant power is applied via a heating circuit. In the event of a clean RTD (solid line), the resulting temperature from the applied constant power is approximately constant over time. However, the temperature of a fouled RTD (broken line) increases over time. As described elsewhere herein, as deposits form on the RTD, the deposits insulate the RTD from the cooling effects of the process fluid. In general, a thicker deposit will result in greater insulating properties, and thus a greater temperature achieved by applying the same power to the RTD.

In some embodiments, the difference in temperature between a clean RTD and an RTD under test when a constant power is applied to each can be used to determine the level of deposit on the RTD under test. Additionally or alternatively, the rate of temperature increase based on a constant applied power can provide information regarding the rate of deposition of a deposit on an RTD, which can be used to determine a level of deposit on the RTD.

With reference to FIGS. 6A-6D, various processes have been described for characterizing a deposit on an RTD. Such processes generally involve heating the RTD via a heating circuit and measuring a temperature of the RTD via a measurement circuit. Changes in the thermal behavior of the RTD (e.g., temperature increase or decay profile, the applied power required to reach a predetermined temperature, the temperature achieved at a predetermined applied power) provide evidence of a deposit forming on the RTD. In some examples, such changes can be used to determine a level of deposit on the RTD.

In various embodiments, a controller can be configured to interface with a heating circuit and a measurement circuit in order to perform one or more of such processes to observe or detect any deposition from a process fluid onto an RTD. In an exemplary implementation with reference to FIGS. 1 and 2, an RTD (e.g., 102a) can be elevated to the operating temperature of a use device 105 via a heating circuit (e.g., 214). Since the deposition of constituents of a process fluid is often temperature dependent, elevating the temperature of the RTD to the operating temperature of the use device can simulate the surface of the use device at the RTD. Accordingly, deposits detected at the RTD can be used to estimate deposits at the use device.

In some examples, the use device becomes less functional when deposits are present. For instance, in a heat exchanger system wherein the use device comprises a heat exchange surface, deposits formed on the heat exchange surface can negatively impact the ability for the heat exchange surface to transfer heat. Accordingly, sufficient depots detected at the RTD can alert a system operator of likely deposits at the heat exchange surface, and corrective action can be taken (e.g., cleaning the heat exchange surface). However, even if the RTD simulating the use device allows a system operator to detect the presence of a deposit at the use device, addressing the detected deposit (e.g., cleaning, etc.) can require costly system downtime and maintenance since the deposition has already occurred. Additionally or alternatively, in some instances, various deposits may not clean well even if removed for a cleaning process, possibly rendering the use device less effective.

Accordingly, in some embodiments, a plurality of RTDs (e.g., 102a-d) can be disposed in a single fluid flow path (e.g., 106) and used to characterize the status of the process fluid and/or the fluid flow system (e.g., 100). With reference to FIG. 1, in an exemplary implementation, use device 105 of the fluid flow system 100 typically operates at operating temperature $T_0$. RTDs 102a-d can be elevated to temperatures more likely to drive deposition of a deposit from the process fluid than $T_0$. For example, various process fluids can include constituents such as calcium and/or magnesium sulfates, carbonates, and/or silicates, and/or other components that can be deposited from the process fluid. Some such process fluids are more prone to produce deposits on higher temperature surfaces when compared to lower temperatures. In some such examples, one or more of the plurality of RTDs 102a-d are elevated to a temperature higher than the typical operating temperature of the use device 105 in order to induce deposits onto the RTDs and to characterize the deposits forming on the RTDs. This also can represent a "worst case" for use device 105 operation when deposit formation is more likely than usual, such as at an unusually high temperature.

For example, with reference to FIG. 3, in an exemplary embodiment, each of RTDs 302a-d is heated to a different elevated characterization temperature via channels A-D, respectively, of the heating circuit 314. In the exemplary embodiment, the characterization temperature of each of the RTDs 302a-d is above a typical operating temperature of a use device of the fluid flow system. In some such examples, the controller 312 controls the heating circuit 314 to maintain the RTDs 302a-d at their respective elevated characterization temperatures. The controller 312 can periodically switch to operate RTDs 302a-d in a measurement mode via the measurement circuit 310 (e.g., using multiplexer 320 and demultiplexer 322 and current sources 330, 332) to ensure the RTDs 302a-d are elevated to the desired characterization temperature.

During operation, after maintaining the RTDs 302a-d at their respective characterization temperatures, the controller 312 can be configured to perform a deposit characterization process such as those described above with respect to any of FIGS. 6A-D. For example, the controller 312 can, after operating an RTD in the heating mode to maintain an elevated temperature, periodically switch between the heating mode and measurement mode and observe changes in the thermal behavior of the RTD. As described with respect to FIGS. 6A-D, periodically switching between the heating mode and the measurement mode can be performed in a variety of ways.

For example, such switching can include switching to a measurement mode for a period of time to observe the temperature decay of the RTD (e.g., as in FIG. 6A) before heating again. Changes in the thermal behavior of the RTD can include a change in time constant demonstrated by the temperature decay. Alternatively, periodically switching between the heating mode and the measurement mode can include increasing the temperature of the RTD while rapidly switching to the measurement mode to sample the temperature of the RTD and back to the heating mode to continue heating (e.g., as in FIG. 6B). Similarly, changes in the thermal behavior of the RTD can include changes in a time constant demonstrated in the temperature increase profile.

In still another example, periodically switching between the heating mode and the measurement mode can include heating the RTD to maintain the RTD at a constant temperature while periodically switching to the measurement mode to confirm the constant temperature is maintained (e.g., as illustrated in FIG. 6C). In such an embodiment, changes in thermal behavior of the RTD can include changes in the amount of power applied by the heating circuit to maintain the temperature of the RTD at the constant temperature. Alternatively, periodically switching between the heating mode and the measurement mode can include heating the RTD using a constant applied power while periodically sampling the temperature of the RTD in the measurement mode (e.g., as illustrated in FIG. 6D). In such an embodiment, changes in the thermal behavior of the RTD can include changes in the temperature achieved by the RTD due to the constant applied amount of power.

As discussed elsewhere herein, observing such changes in the thermal behavior of an RTD can be indicative of, and used to determine, a level of deposit on the RTD. Thus, in some examples, the controller 312 can perform any of such processes on the plurality of RTDs 302a-d that have been elevated to different temperatures to characterize the level of deposit on each of the RTDs 302a-d. In some such examples, the controller 312 characterizes the deposit level at each of the RTDs 302a-d individually via corresponding channels A-D in the multiplexer 320 and demultiplexer 322.

The controller 312 can be configured to associate the level of deposit of each RTD with its corresponding characterization temperature. That is, the controller 312 can determine a level of deposit at each of the RTDs 302a-d and associate the level of deposit with the initial characterization temperature of each of the respective RTDs 302a-d. The associated deposit levels and operating temperatures can be used to characterize a temperature dependence of deposition on surfaces in the fluid flow system. If the typical operating temperature of the use device (e.g., a heat exchanger surface) is lower than the characterization temperatures of the RTDs 302a-d, and deposits are driven by increased temperature, the use device will tend to have less deposit than the RTDs 302a-d. Moreover, the temperature dependence of deposition characterized by the RTD operation can be used to infer the likelihood of deposits forming on the use device.

Additionally or alternatively, periodically observing the depositions on the various RTDs operating at different characterization temperatures can provide information regarding general increases or decreases in the occurrence of depositions. Such changes in deposition characteristics of the process fluid can be due to a variety of factors affecting the fluid flow system, such as a change in the temperature or concentration of constituents in the process fluid.

In an exemplary operation, an increase in deposition and/or deposition rate detected from the characterization RTDs can be indicative of a deposit condition for the use device, in which deposits forming on the use device during normal operation become more likely. The detection of a deposit condition can initiate subsequent analysis to determine the cause of increased deposition, such as measuring one or more parameters of the process fluid. In some instances, this can be performed automatically, for example, by the controller.

Additionally or alternatively, one or more parameters of the process fluid can be adjusted to reduce the deposits deposited from the process fluid into the fluid flow system and/or to eliminate the deposits that have already accumulated. For instance, a detected increase in deposition can cause an acid or other cleaning chemical to be released to attempt to remove the deposit. Similarly, in some examples, a chemical such as an acid, a scale inhibitor chemical, a scale dispersant, a biocide (e.g., bleach), or the like can be added to the process fluid to reduce the likelihood of further deposition.

In some examples, an increase in deposition (e.g., scale) over time can be due to the absence of or reduction in a typical process fluid constituent (e.g., a scale inhibitor and/or a scale dispersant), for example, due to equipment malfunction or depletion of a chemical. Reintroducing the constituent into the process fluid can act to reduce the amount of deposition from the process fluid into the fluid flow system. Additionally or alternatively, various fluid properties that can impact the likelihood of deposit formation can be measured via one or more sensors (e.g., 111) in the fluid flow system, such as fluid operating temperature, pH, alkalinity, and the like. Adjusting such factors can help to reduce the amount and/or likelihood of deposition.

In various embodiments, any number of steps can be taken in response to address an increase in detected deposition or other observed deposition trends. In some embodiments, the controller is configured to alert a user of changes or trends in deposits. For example, in various embodiments, the controller can alert a user if deposit rates, levels, and/or changes therein meet a certain criteria. In some such examples, criteria can be temperature dependent (e.g., a deposit level or rate occurring at an RTD with a certain characterization temperature) or temperature independent. Additionally or alternatively, the controller can alert a user if determined properties of the process fluid satisfy certain criteria, such as too low or too high of a concentration of a fluid constituent (e.g., that increase or decrease likelihood of deposits) and/or various fluid properties that may impact the amount and/or likelihood of deposition.

In some such examples, alerting the user is performed when the system is potentially trending toward an environment in which deposits may being to form on the use device so that corrective and/or preventative action can be taken before significant deposits form on the use device. In some examples, an alert to a user can include additional information, such as information regarding properties of the process fluid flowing through the system, to better help the user take appropriate action. Additionally or alternatively, in some embodiments, the controller can be configured to interface with other equipment (e.g., pumps, valves, etc.) in order to perform such action automatically.

In some systems, certain deposits become more likely as the deposit surface temperature increases. Thus, in some embodiments, RTDs (e.g., 302a-d) can be heated to temperatures above the typical operating temperatures of a use device in order to intentionally induce and monitor deposits from the process fluid can help to determine situations in which the use device is at risk for undesired deposits. In some such embodiments, observing deposition characteristics on one or more RTDs that are operating at a temperature higher than a typical temperature of the use device can be used to determine deposition trends or events at certain surface temperature while minimizing the risk of actual deposition on the use device. In some instances, elevating different RTDs to different temperature provides the controller with information regarding the temperature dependence of deposit formation in the fluid flow system, and can be further used to characterize deposit formation in the fluid flow system.

After repeated or prolonged characterization in which the RTDs are heated to induce deposits, the RTDs may eventually become too coated for effective characterization. In some such embodiments, the plurality of RTDs (e.g., 102a-d) can be removed from the system and cleaned or replaced without disrupting operation of the system or use device. For example, with reference to FIG. 1, the RTDs 102a-d can be mounted to a sample holder 104 that is easily removable from the system 100 for servicing the RTDs 102a-d. Thus, in some embodiments, cleaning or replacing the characterization RTDs can be performed with much lower cost and less downtime than having to service the use device itself.

In some examples, the likelihood of deposits forming within a fluid flow system can be considered a deposit potential of the system. In various embodiments, the deposit potential can be a function of surface temperature of an object within the fluid flow system. In other examples, the deposit potential may be associated with a particular use device within the system. In some systems, the deposit potential can be used as a metric for observing the absolute likelihood of deposits forming within the system. Additionally or alternatively, the deposit potential can be used as a metric for observing change in the deposit conditions within the fluid flow system. In some such examples, the absolute deposit potential need not necessarily correspond to a deposit condition, but changes in the deposit potential may be indicative of increased likelihood of a deposit condition, for example.

Figure 7:
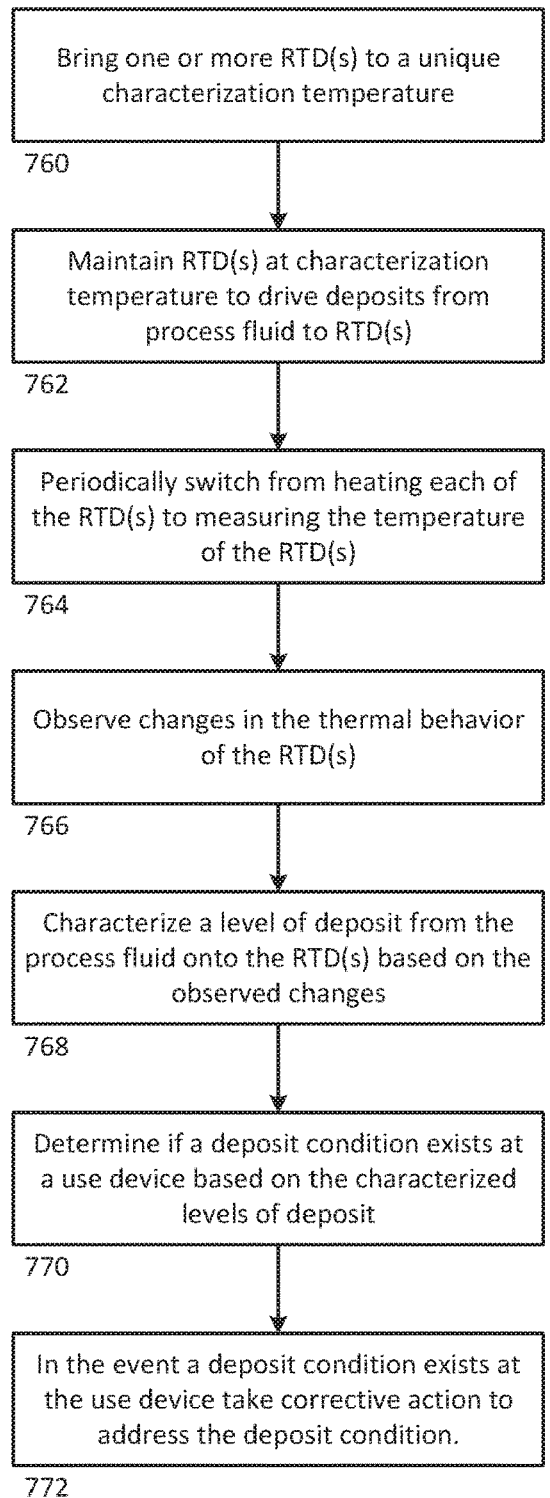
FIG. 7 is a process-flow diagram illustrating an exemplary process for mitigating deposits from a process fluid onto a use device in a fluid flow system.

FIG. 7 is a process-flow diagram illustrating an exemplary process for assessing the deposit potential of a process fluid onto a use device in a fluid flow system. The method includes bringing one or more RTD(s) to a unique characterization temperature (760) and maintaining the RTD(s) at the characterization temperatures to drive deposits from the process fluid onto the RTD(s) (762). This can be performed, for example, by operating the RTD(s) in a heating mode using a heating circuit as described elsewhere herein. In some examples, at least one of the characterization temperatures is higher than an operating temperature of the use device. It will be appreciated that, bringing one or more RTD(s) to a characterization temperature can include operating one or more RTD(s) in thermal equilibrium with the process fluid flowing through the fluid flow system. That is, the characterization temperature for one or more RTDs can be approximately the same temperature as the process fluid flowing through the fluid flow system.

The method further includes periodically switching the RTD(s) from the heating mode to a measurement mode to measure the temperature of the RTD(s) (764) and observing changes in the thermal behavior of the RTD(s) (766). This can include, for example, processes as described with respect to FIGS. 6A-D. The observed changes can be used to characterize a level of deposit from the process fluid onto each of the one or more RTD(s) (768). This can include, for example, determining a time constant for a fitting function of measured temperature decay and observing changes to the time constant at different measurement times. Changes in the time constant can be representative of deposits forming on the RTD and altering the thermal behavior of the RTD. In some examples, characterizing the level of deposit can include comparing decay profiles for RTDs operating at difference characterization temperatures (e.g., a heated RTD and an unheated RTD).

In addition to a deposit thickness, additional characterization of the levels of deposit can include determining a likely deposited material in the system. Comparing the thermal decay profiles for heated and unheated or only slightly heated RTDs, the nature of the deposit can be determined. For example, in some cases, sedimentation and/or biofilm (e.g., microbial growth) deposits are generally unaffected by the surface temperature, while scaling effects will be enhanced at higher temperatures. Thus, the characterization temperature dependence of the thermal decay profiles can be used to characterize the type of deposits present at the RTDs and within the fluid flow system.

The method can further include determining if a deposit condition exists at the use device. This can include, for example, monitoring the deposition levels and/or rates at the plurality of RTD(s) over time to observe deposition trends. In some examples, certain rates of deposition or increases in rates of deposition can indicate a deposit condition in which deposits forming on the use device become more likely. In some such examples, levels of deposit, rates of deposit, and/or changes therein at an RTD can be analyzed in combination with its associated characterization temperature to determine if a deposit condition exists. Additionally or alternatively, analyzing the relationship of such data (e.g., levels of deposit, rates of deposit, and/or changes therein) with respect to temperature (e.g., at RTD(s) having difference characterization temperatures) can be used to detect a deposit condition.

In some examples, monitored deposit levels, deposit rates, and/or other data such as fluid properties (e.g., temperature, constituent concentrations, pH, etc.) can be used to determine a deposit potential of the process fluid on to the use device. In various embodiments, the deposit potential meeting a predetermined threshold and/or changing by a predetermined amount can be used to detect the presence of a deposit condition.

In the event of a deposit condition, the method can include taking corrective action to address the deposit condition (772). The corrective action can include a variety of actions, such as introducing or changing the dose of one or more chemicals in the process fluid, changing the temperature of the process fluid, alerting a user, adjusting the use device for the process fluid (e.g., a heat load on a heat exchanger), increasing a rate of blowdown, and/or other actions that can affect the deposition characteristics of the process fluid. In an exemplary embodiment, deposition characterization can include determining the likely deposited material, such as scale, biofilm, or the like.

In some such embodiments, the corrective action (e.g., 772) can be specifically taken to address the determined deposit material. For instance, a scale inhibitor can be added or increased due to a detected scaling event. However, if the deposition characterization is representative of a biofilm rather than scale, a biocide can be added or increased. Such corrective actions can be performed automatically by the system. Additionally or alternatively, the system can signal to a user to take corrective action to address the deposit condition.

In some embodiments in which the fluid flow system can receive fluid from a plurality of fluid sources (e.g., selectable input sources), the corrective action can include changing the source of fluid input into the system. For instance, in an exemplary embodiment, a fluid flow system can selectively receive an input fluid from a fresh water source and from an effluent stream from another process. The system can initially operate by receiving process fluid from the effluent stream. However, in the event of a detected or potential deposit condition, the source of fluid can be switched to the fresh water source to reduce the possible deposit materials present in the process fluid. Switching the source of fluid can include completely ceasing the flow of fluid from one source and starting the flow of fluid from a different source. Additionally or alternatively, switching sources can include a mixture of the original source (e.g., the effluent stream) and the new source(s) (e.g., the fresh water). For example, in some embodiments, a desired blend of fluid from different input sources (e.g., 50% from one source and 50% from another source) can be selected.

In a similar implementation, in some embodiments, the corrective action can include temporarily stopping flow from a single source (e.g., an effluent source) and providing a process fluid from a different source (e.g., fresh water). The new source of fluid can be used temporarily to flush potential deposit materials from the system before excessive deposit can occur. In some examples, once such materials have been flushed from the system (e.g., via fresh water), the source of the process fluid can be switched back to the original source (e.g., the effluent stream). In some examples, flushing the fluid from the system can be done while operating the use device in the system. In other examples, when certain deposit conditions and/or likelihoods are detected (e.g., a certain deposit potential is reached), flow to the use device can be stopped and the fluid in the system can be directed to a drain to rid the system of such fluid. The system can then direct fluid back to the use device from either fluid source or a combination thereof.

In still another implementation, as described elsewhere herein, a default input fluid can be the combined flow of fluid from each of a plurality of available sources. In the event of detected deposit conditions, one or more of the fluid sources can be closed off from the system (e.g., via a shutoff valve). In some examples, systems can include one or more auxiliary sensors configured to monitor one or more parameters of the fluid flowing into the system from each input source, such as a conductivity sensor, concentration sensor, turbidity sensor, or the like. Data from such auxiliary sensors can be used to determine which of the input sources is/are contributing to the deposit condition. Such fluid sources can then be prevented from contributing to the fluid flowing through the system.

Blocking, switching between, and/or combining process fluid input sources can be performed, for example, via one or more valves arranged between the source(s) and the fluid flow system. In various embodiments, the valves can be manually and/or automatically controlled to adjust the source(s) of the input fluid. For example, in some embodiments, a detected deposit condition can cause a controller in communication with one or more such valves to actuate such valves to adjust the source of fluid flowing into the system. Alternatively, the controller can indicate to the user that corrective action should be performed, and the user can actuate such valves to adjust the source of fluid to the system.

As described elsewhere herein, one or more fluid input sources can include one or more RTDs disposed therein. Such RTD(s) can be used to characterize deposit conditions for each of the plurality of fluid sources individually. Accordingly, if one fluid source is exhibiting a deposit condition, one or more corrective actions can include performing an action to affect the fluid flowing into the system from that source (e.g., adjusting a parameter of the fluid) and/or blocking the fluid from flowing into the system (e.g., via a valve). In some examples, each input fluid source includes one or more such RTDs so that each source can be characterized individually. In some such embodiments, one or more RTDs can additionally be positioned in the fluid flow path after fluid from each of the fluid sources are combined so that the composite fluid can also be characterized separately from each of the individual sources.

In general, taking one or more corrective actions (e.g., step 772) can act to reduce the rate of deposition at the use device. Thus, in some such embodiments, the corrective action acts as a preventative action for preventing undesirable deposits from forming on the use device. This can prolong the operability of the use device while minimizing or eliminating the need to shut down the system in order to clean deposits from the use device.

In some embodiments the taken and/or suggested corrective action can be based on data received from one or more additional sensors (e.g., 111). For instance, in some embodiments, reduction in a scale inhibitor (e.g., detected via a scale inhibitor introduction flow rate meter and/or a scale inhibitor concentration meter) contributes to a deposit condition in the system. Thus, the corrective action can include replenishing a supply of scale inhibitor. Similarly, in some examples, the presence of excess deposit material (e.g., calcium detected by a concentration meter) contributes to a deposit condition. Corresponding corrective action can include introducing or increasing the amount of a scale inhibitor into the system. Additionally or alternatively, a corrective action can include changing phosphate levels in the fluid. For example, phosphate deposits accumulating in the system can result in reducing the flow of a phosphorus-containing chemical or phosphate deposition catalyst. In other examples, the addition of phosphate-containing fluids may inhibit other deposits from forming. In some such examples, such phosphate- or phosphorus-containing fluids can be added or increased.

Appropriate corrective actions can be determined, in some embodiments, based on the characterized levels of deposits (e.g., at step 768). For example, greater deposition rates and/or deposit potentials can result in greater amounts of scale inhibitor to be released into the system to prevent deposits from forming. Additionally or alternatively, characterizations in the type of deposits forming (e.g., by comparing thermal decay profiles at different temperatures) can influence which corrective actions are taken. For example, if characterization of the deposit levels indicates that the deposits are generally sedimentation rather than scaling, releasing scale inhibitor chemicals may not be a useful action, and other, more appropriate action may be taken.

Various embodiments have been described. Such examples are non-limiting, and do not define or limit the scope of the invention in any way. Rather, these and other examples are within the scope of the following claims.

The invention claimed is:

1. A method for characterizing the level of deposits from a fluid in a fluid flow system comprising:
   operating each of a plurality of resistance temperature detectors (RTDs) in a heating mode of operation in order to heat the RTD to a corresponding characterization temperature and induce a deposit from the fluid to form on a surface of at least one of the plurality of RTDs in fluid communication with the fluid, each of the RTDs being heated to a unique characterization temperature;
   for each of the plurality of RTDs:

periodically switching the RTD between the heating mode and a measurement mode in order to measure the temperature of the RTD, observing changes in the thermal behavior of the RTD in one or both of the heating mode and the measurement mode, and characterizing a level of deposit from the process fluid onto the RTD based on the observed changes; and characterizing a temperature dependence of deposition in the fluid flow system based on the characterized level of deposit for each of the plurality of RTDs.

2. The method of claim 1, wherein, for at least one of the plurality of RTDs:

observing changes in the thermal behavior of the RTD comprises, after operating the RTD in the heating mode, switching the RTD to operate in the measurement mode and measuring the rate at which the temperature of the RTD changes; and wherein characterizing the level of deposit from the process fluid onto the RTD comprises associating the rate the temperature of the RTD decreases with a level of deposit from the process fluid.

3. The method of claim 1, wherein, for at least one of the plurality of RTDs:

operating the RTD in the heating mode comprises operating the RTD at a fixed operating power;

periodically switching between the heating mode and the measurement mode further comprises switching from the heating mode to the measurement mode, measuring the temperature of the RTD, and switching back to the heating mode;

observing changes in the behavior of the RTD comprises observing the change in temperature over time while operating the RTD at the fixed operating power; and characterizing a level of deposit from the process fluid comprises associating the rate of change in temperature of the RTD at the fixed operating power with a level of deposit from the process fluid.

4. The method of claim 1, wherein, for at least one of the plurality of RTDs:

observing changes in the behavior of the RTD comprises measuring the rate at which the temperature of the RTD increases due to the operating the RTD in the heating mode; and characterizing the level of deposit from the process fluid onto the RTD comprises associating the rate the temperature of the RTD rises with a level of deposit from the process fluid.

5. The method of claim 1, wherein, for at least one of the plurality of RTDs:

operating the RTD in a heating mode of operation comprises elevating the RTD to a fixed temperature;

periodically switching between the heating mode and the measurement mode further comprises switching from the heating mode to the measurement mode to confirm the temperature of the RTD is the fixed temperature;

observing changes in the behavior of the RTD comprises observing a change in the electrical power required to elevate the RTD to the fixed temperature; and characterizing the level of deposit from the process fluid comprises associating the rate of change of applied power required to elevate the RTD to the fixed temperature with a level of deposit from the process fluid.

6. The method of claim 5, wherein the fixed elevated temperature corresponds to an operating temperature of equipment in the process fluid flow path.

7. The method of claim 1, further comprising, if the characterized level of deposit for at least one of the plurality of RTDs meets a predetermined condition, performing a corrective action.

8. The method of claim 7, wherein the corrective action comprises one or more actions from the group consisting of: adding a chemical to the fluid, changing the dose of a chemical in the fluid, stopping the flow of a fluid from one or more fluid sources, increasing the rate of blowdown, changing the temperature of the process fluid, adjusting a use device toward with the process fluid flows, and alerting a user.

9. A fluid flow system for directing a fluid toward a use device comprising:

a plurality of resistance temperature detectors (RTDs), the plurality of RTDs including a first RTD and a second RTD;

a heating circuit in electrical communication with the plurality of RTDs and capable of applying electrical power to the RTDs;

a measurement circuit in communication with the plurality of RTDs;

a controller in communication with the heating circuit and the measurement circuit and capable of operating each of the plurality of RTDs in a heating mode via the heating circuit and a measurement mode via the measurement circuit, the controller being configured to:

operate one or more of the plurality of RTDs in the heating mode of operation in order to maintain each of the one or more RTDs at a characterization temperature to induce a deposit from the process fluid to form on at least one of the one or more RTDs, at least one of the characterization temperatures being higher than a typical operating temperature of the use device, the operating the one or more of the plurality of RTDs in the heating mode of operation comprising maintaining the first RTD at a first characterization temperature and maintaining the second RTD at a second characterization temperature different from the first characterization temperature;

for each of the one or more RTDs, periodically switch the RTD between the heating mode and the measurement mode in order to measure the temperature of the RTD, observe changes in the thermal behavior of the RTD in one or both of the heating mode and the measurement mode, and characterize a level of deposit from the process fluid onto the RTD based on the observed changes;

determine a temperature-dependent deposition profile based on the characterized level of deposit of each of the one or more RTDs; and determine if a deposit condition exists for the use device based on the deposition profile.

10. The system of claim 9, wherein the controller is further configured to determine a critical temperature associated with the formation of a deposit on at least one of the one or more RTDs from the process fluid.

11. The system of claim 9, wherein, if it is determined that a deposit condition exists for the use device, performing one or more corrective actions to address the deposit condition.

12. The system of claim 11, wherein at least one of the one or more corrective actions are selected from the group consisting of: introducing a chemical into the fluid, changing the amount of a chemical added to the fluid, changing the temperature of the fluid, alerting a user of a deposit condition, adjusting one or more operating conditions of the use device, and increasing the rate of blowdown of the system.

13. The system of claim 11, further comprising an input to the fluid flow system in selective fluid communication with a plurality of fluid sources; and wherein
the one or more corrective actions comprises adjusting the source of fluid to the system.

14. The system of claim 13, wherein adjusting the source of the fluid to the system comprises stopping the flow of a fluid from one or more of the plurality of fluid sources.

15. A deposit analysis system comprising:
a plurality of resistance temperature detectors (RTDs) positioned in a fluid flow system such that a surface of each of the plurality of RTDs is in thermal communication with the fluid flowing through the fluid flow system;
a heating circuit in communication with each of the plurality of RTDs and being configured to apply a variable amount of electrical power to each of the RTDs in order to affect the temperature thereof;
a measurement circuit in communication with each of the plurality of RTDs and being configured to output a signal representative of the temperature thereof; and
a controller in communication with the heating circuit and the measurement circuit and configured to:
for each of the plurality of RTDs:
heat the RTD to a characterization temperature via the heating circuit, each of the plurality of RTDs being heated to a different characterization temperature;
stop heating the RTD;
characterize the temperature change of the RTD over time due to thermal conduction of heat from the RTD to the fluid flowing through the fluid flow system via the measurement circuit; and
determine a level of deposit formed on the surface of the RTD from the fluid based on the characterized temperature change; and
characterize a temperature dependence of deposition in the fluid flow system based on the determined level of deposit for each of the plurality of RTDs.

16. The system of claim 15, wherein controller is configured to maintain at least one of the plurality of RTDs at a characterization temperature above a typical operating temperature of a system use device to induce deposit onto the surface of the RTD.

17. The system of claim 15, wherein the measurement circuit comprises a multiplexer and a demultiplexer in communication with each of the plurality of RTDs, and wherein the multiplexer and demultiplexer are used to measure the temperature of each of the plurality of RTDs one at a time.

18. The system of claim 15, wherein characterizing the temperature change of the at least one of the plurality of RTDs over time comprises fitting temperature data associated with the at least one of the RTDs over time to a function, and wherein a fitting parameter of the function is representative of the degree of deposit on the surface of the at least one RTD.

19. The system of claim 18, wherein function comprises an exponential function.

20. The system of claim 19, wherein the fitting function comprises a double exponential function having a first part and a second part, and wherein
the first part of the double exponential function represents heat conducted from the at least one RTD to the fluid sample;
the second part of the double exponential function represents heat conducted from the at least one RTD to other system components; and
the fitting parameter representative of the degree of deposit is present in the first part of the double exponential function and not in the second part of the double exponential function.

* * * * *